United States Patent
Louie et al.

(10) Patent No.: US 12,402,925 B2
(45) Date of Patent: Sep. 2, 2025

(54) TARGETING SYSTEM FOR A PERIPROSTHETIC BONE PLATE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Stephen Louie, Cordova, TN (US); Nicholas S. Ritchey, Collierville, TN (US); Nathaniel Kelley Grusin, Germantown, TN (US); Sandy Todd Strachan, Glen, MS (US); William M. Ricci, New York, NY (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 206 days.

(21) Appl. No.: 18/276,363

(22) PCT Filed: Feb. 9, 2022

(86) PCT No.: PCT/US2022/015727
§ 371 (c)(1),
(2) Date: Aug. 8, 2023

(87) PCT Pub. No.: WO2022/173776
PCT Pub. Date: Aug. 18, 2022

(65) Prior Publication Data
US 2024/0115299 A1    Apr. 11, 2024

Related U.S. Application Data

(60) Provisional application No. 63/148,492, filed on Feb. 11, 2021.

(51) Int. Cl.
*A61B 17/80* (2006.01)
*A61B 17/16* (2006.01)
(Continued)

(52) U.S. Cl.
CPC ........ *A61B 17/808* (2013.01); *A61B 17/1728* (2013.01); *A61B 17/8057* (2013.01);
(Continued)

(58) Field of Classification Search
CPC ... A61B 17/1728; A61B 17/80; A61B 17/808; A61B 17/8057; A61B 17/8061;
(Continued)

(56) References Cited

U.S. PATENT DOCUMENTS 8,187,281 B2    5/2012    Cresina
9,730,711 B2    8/2017    Wolf
(Continued)

FOREIGN PATENT DOCUMENTS

EP    3375392 A1    9/2018
WO    2021087024 A1    5/2021

OTHER PUBLICATIONS

International Search Report and Written Opinion for the Application No. PCT/US2022/015727, mailed Jul. 4, 2022, 13 pages.
(Continued)

*Primary Examiner* — Marcela I. Shirsat
(74) *Attorney, Agent, or Firm* — KDW Firm PLLC

(57) ABSTRACT

A targeting system is disclosed. In use, the targeting system is configured to target (e.g., aim, locate, etc.) a fastener opening in a bone plate, more particularly, a variable angled fastener opening formed in a periphery of a periprosthetic bone plate. In one embodiment, the targeting system includes an alignment guide including a plurality of combo-slots for targeting a plurality of openings formed in the periprosthetic bone plate. In addition, the targeting system
(Continued)

includes a plug configured to be positioned within the combo-slots formed in the alignment guide. In use, positioning the plug into the combo-slot formed in the alignment guide transforms the combo-slot into a substantially circular hole or opening with a predefined trajectory aligned with one of the variable angled openings formed in the periphery of the periprosthetic bone plate thereby defining a trajectory from the alignment guide to the variable angled opening.

22 Claims, 16 Drawing Sheets

(51) Int. Cl.
 A61B 17/17 (2006.01)
 A61B 17/56 (2006.01)
 A61B 17/58 (2006.01)
 A61B 17/90 (2006.01)
(52) U.S. Cl.
 CPC ....... *A61B 17/1657* (2013.01); *A61B 17/1662* (2013.01); *A61B 17/1732* (2013.01); *A61B 17/1739* (2013.01); *A61B 17/56* (2013.01); *A61B 2017/564* (2013.01); *A61B 17/58* (2013.01); *A61B 17/8061* (2013.01); *A61B 17/90* (2021.08)

(58) Field of Classification Search
 CPC ......... A61B 17/90; A61B 17/56; A61B 17/58; A61B 17/1657; A61B 17/1662; A61B 17/17; A61B 17/1732; A61B 17/1739; A61B 2017/564
 USPC .............................. 606/280, 70–71, 281–299
 See application file for complete search history.

(56) References Cited

U.S. PATENT DOCUMENTS

| | | | |
|---|---|---|---|
| 2005/0049594 A1* | 3/2005 | Wack ................. | A61B 17/1728 606/281 |
| 2006/0095044 A1 | 5/2006 | Grady | |
| 2008/0132900 A1* | 6/2008 | Prien ................. | A61B 17/1728 606/96 |
| 2011/0166573 A1* | 7/2011 | Wenk ................. | A61B 17/1728 606/71 |
| 2012/0089144 A1* | 4/2012 | Murner .............. | A61B 17/1728 606/70 |
| 2018/0289402 A1* | 10/2018 | Lueth ................. | A61B 17/8061 |
| 2022/0395303 A1 | 12/2022 | Rakes | |

OTHER PUBLICATIONS

MIS Radiolucent Targeting Device NCB® PeriprostheticFemur Plate System—Surgical Technique Brochure— © 2013 Zimmer, Inc.

* cited by examiner

TARGETING SYSTEM FOR A PERIPROSTHETIC BONE PLATE

CROSS-REFERENCE TO RELATED APPLICATIONS

This application is a National Phase filing of International Application No. PCT/US2022/015727, filed Feb. 9, 2022, which is a non-provisional of, and claims the benefit of the filing date of, U.S. provisional patent application No. 63/148,492, filed Feb. 11, 2021, entitled "Targeting System for a Periprosthetic Bone Plate," the entirety of each application is incorporated by reference herein.

TECHNICAL FIELD

The present disclosure is directed to a targeting system for locating a fastener opening in a bone plate, and more specifically to a targeting system arranged and configured to assist with targeting a fastener opening in a periprosthetic bone plate.

BACKGROUND

Bone fractures are often repaired by securing an orthopedic implant or device to one or more patient's bone(s), bone portions, bone fragments, etc. (used interchangeably without the intent to limit). For example, it is not uncommon for a patient to receive an orthopedic knee prosthesis, an orthopedic hip prosthesis, an intramedullary ("IM") nail, etc. to repair one or more fractures in a patient's bone.

On occasion a bone fracture may occur in the area surrounding a previous surgically implanted orthopedic implant or device. For example, a fracture may occur during a surgical implant procedure. Alternatively, however, as is the case in most scenarios, a periprosthetic fracture may occur in a patient years after the original surgical implant procedure. In some cases, a surgically implanted orthopedic implant may predispose a patient's bone to later fractures.

Whatever the cause, periprosthetic fractures surrounding a previous surgically implanted orthopedic implant pose unique fixation challenges. For example, the previous surgically implanted orthopedic device or implant may interfere with the placement of a subsequently implanted orthopedic bone fixation plate.

For example, in one scenario, a periprosthetic hip fracture may occur adjacent or around a previous surgically implanted hip replacement prosthesis. As the number of hip replacement prosthesis has increased, so too has the number of periprosthetic fractures associated therewith. Once a fracture occurs in the area surrounding a previous surgically implanted hip replacement prosthesis, treatment may be complicated by osteoporosis, defects in the bone, and the presence of the previous surgically implanted hip replacement prosthesis. For example, stems, rods, screws, and cement associated with the previous surgically implanted hip replacement prosthesis may block the patient's medullary canal, preventing intramedullary fixation of the subsequent fracture. Moreover, stems and rods may also block screw fixation through the medullary canal to secure a subsequent bone plate to the patient's bone. As a result, periprosthetic fractures and the corresponding techniques for treating periprosthetic fractures are generally more difficult, with limited options.

Nevertheless, periprosthetic fractures require treatment. For example, an unstable periprosthetic fracture may require surgical stabilization and/or implant replacement to restore function. Surgical stabilization may include implantation of a bone fixation plate to secure the adjacent sections of the fractured bone to facilitate healing, which may occur with or without implant replacement.

It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is a targeting system arranged and configured to target a variable angled opening in a periprosthetic bone plate to facilitate insertion of a bone fastener into the variable angled opening. In accordance with one or more features of the targeting system, the targeting system includes an alignment guide and a plug positionable within a combo-slot formed in the alignment guide. During use, the plug may be positioned within an enlarged central portion of the combo-slot to define or create a defined trajectory to a variable angled opening formed in the periprosthetic bone plate. As a result, a surgical instrument such as, for example, a trocar, a drill guide, and/or a screw guide can be easily aligned with the variable angled opening formed in the periprosthetic bone plate. In one embodiment, a distal end of the surgical instrument can be coupled to the variable angled opening formed in the periprosthetic bone plate. Thereafter, the plug can be removed from the combo-slot formed in the alignment guide to enable additional freedom in positioning the surgical instrument relative to the variable angled opening formed in the periprosthetic bone plate.

Thus arranged, the targeting system enables a surgeon to accurately locate the variable angled openings formed in the periprosthetic bone plate. In addition, the targeting system enables a surgeon to adjust the trajectory of the drill within the range provided by the variable angled opening formed in the periprosthetic bone plate while preventing the drill guide from dislodging from the periprosthetic bone plate.

In one embodiment, the targeting system is arranged and configured to target a fastener opening in a periprosthetic bone plate. More specifically, the targeting system is arranged and configured to target a smaller diameter, variable angled opening formed in a periphery of a periprosthetic bone plate. The targeting system comprises an alignment guide including a plurality of combo-slots for targeting a plurality of openings formed in the periprosthetic bone plate, a device arranged and configured to couple the alignment guide to the periprosthetic bone plate, and a plug arranged and configured to be positioned within one of the plurality of combo-slots formed in the alignment guide, wherein positioning the plug into the combo-slot formed in the alignment guide transforms the combo-slot into a circular opening with a predefined trajectory aligned with one of the plurality of variable angled openings formed in the periprosthetic bone plate (e.g., defines an opening through the alignment guide having a defined trajectory to the variable angled opening formed in the periprosthetic bone plate).

In one embodiment, the combo-slot includes an enlarged central portion and an elongated slot extending from the enlarged central portion, the plug being positioned within the enlarged central portion.

In one embodiment, the device includes a targeter handle including a distal end arranged and configured to couple to the periprosthetic bone plate and a proximal end arranged and configured to couple to the alignment guide.

In one embodiment, the distal end includes an elongated plate-like end portion including a distal surface arranged and configured to contact a top surface of the periprosthetic bone plate and a projection extending from the distal surface, the projection being arranged and configured to be positioned within an opening formed in the periprosthetic bone plate.

In one embodiment, the elongated plate-like end portion includes one or more openings arranged and configured to align with one or more locking screw openings formed in the periprosthetic bone plate, and one or more contours formed along a periphery of the elongated plate-like end portion arranged and configured to facilitate access to the variable angled openings formed in the periprosthetic bone plate.

In one embodiment, the proximal end of the targeter handle includes a bearing surface and a proximal projection, the bearing surface being arranged and configured to enable a bottom surface of the alignment guide to be seated thereon, the proximal projection being arranged and configured to extend through an opening formed in the alignment guide.

In one embodiment, the plug includes a distal end portion arranged and configured to be positioned within the enlarged central portion of the combo-slot formed in the alignment guide.

In one embodiment, the plug includes a flexible, cantilevered arm extending from a proximal end thereof towards a distal end thereof, the distal end portion of the flexible, cantilevered arm being arranged and configured to engage the enlarged central portion of the combo-slot formed in the alignment guide to couple the plug to the alignment guide. For example, in one embodiment, the cantilevered arm includes a laterally extending projection arranged and configured to mate with a keyway formed in the enlarged central portion of the combo-slot formed in the alignment guide.

In one embodiment, the distal end portion of the plug includes a circular projection arranged and configured to be received within the enlarged central portion of the combo-slot formed in the alignment guide.

In one embodiment, the circular projection includes a notch formed therein, the notch being arranged and configured to correspond with a radius of the elongated slotted portion of the combo-slot, wherein, with the circular projection positioned within the enlarged central portion of the combo-slot, the notch partially defines the opening.

In one embodiment, the circular projection of the distal end portion of the plug includes a slot extending from a distal end thereof, the slot defining first and second flexible arms.

In one embodiment, the first and second flexible arms are arranged and configured with a kick to bias the plug toward a centerline of the alignment guide.

In one embodiment, the targeting system further comprises a surgical instrument selected from one of a trocar, a drill guide, a screw guide, or a combination thereof, wherein the surgical instrument is arranged and configured to engage the variable angled opening formed in the periprosthetic bone plate.

In one embodiment, the plug is selectively removable from the variable angled opening formed in the periprosthetic bone plate to enable additional freedom in positioning the surgical instrument relative to the variable angled opening formed in the periprosthetic bone plate.

In one embodiment, the targeting system further comprises the periprosthetic bone plate. In one embodiment, the periprosthetic bone plate includes a head portion, a shaft portion, an upper surface, a lower surface, a central longitudinal axis, and an outer periphery surface. The shaft portion includes a plurality of threaded locking screw openings arranged and configured to receive a plurality of locking screws, respectively, and a plurality of variable angled openings arranged and configured to receive a plurality of variable angled screws, respectively, the plurality of variable angled openings are positioned along the outer periphery surface of the shaft portion while the plurality of locking screw openings are positioned closer to the central longitudinal axis of the shaft portion.

In one embodiment, the plurality of threaded locking screw openings include a first diameter and the plurality of variable angled openings include a second diameter, the first diameter being larger than the second diameter. For example, in one embodiment, the threaded locking screw openings may be sized and configured to receive, for example, 4.5 mm locking screws. The variable angled openings may be sized and configured to receive, for example, 3.5 mm bone screws.

In one embodiment, a method of percutaneously locating a fastener opening formed in a periprosthetic bone plate is disclosed. The method comprising positioning the periprosthetic bone plate adjacent to a patient's fractured bone, the patient's bone including a previous surgically implanted orthopedic implant. Coupling an alignment guide to the periprosthetic bone plate, the alignment guide including a plurality of combo-slots formed therein. Inserting a plug into one of the plurality of combo-slots formed in the alignment guide, the plug transforming the combo-slot into a hole with a predefined trajectory aligned with one of a plurality of variable angled openings formed in a periphery of the periprosthetic bone plate. Inserting a surgical instrument through the hole defined by the combo-slot and the plug, In one embodiment, the surgical instrument is inserted until a distal end thereof engages the variable angled opening formed in the periprosthetic bone plate.

In one embodiment, the method further comprises removing the plug from the combo-slot formed in the alignment guide to allow the surgical instrument to freely move.

In one embodiment, the alignment guide is coupled to the periprosthetic bone plate via a targeter handle having a distal end coupled to the periprosthetic bone plate and a proximal end extending through an opening formed in the alignment guide.

In one embodiment, the alignment guide is coupled to the periprosthetic bone plate prior to positioning the periprosthetic bone plate adjacent to the patient's fractured bone.

In one embodiment, the alignment guide is coupled to the periprosthetic bone plate after positioning the periprosthetic bone plate adjacent to the patient's fractured bone.

Embodiments of the present disclosure provide numerous advantages. For example, when used in combination with a periprosthetic bone plate including a plurality of variable angled openings, and more particularly, a plurality of smaller diameter, variable angled openings, positioned along and/or adjacent to an outer periphery surface of the periprosthetic bone plate, the targeting system facilitates easier targeting and insertion of a fastener into the smaller diameter, variable angled openings. More specifically, the targeting system is arranged and configured to create a defined trajectory to the variable angled opening so that surgical instruments can be properly positioned. Thereafter, the targeting system enables the surgical instruments to be freely positioned around the variable angled opening.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
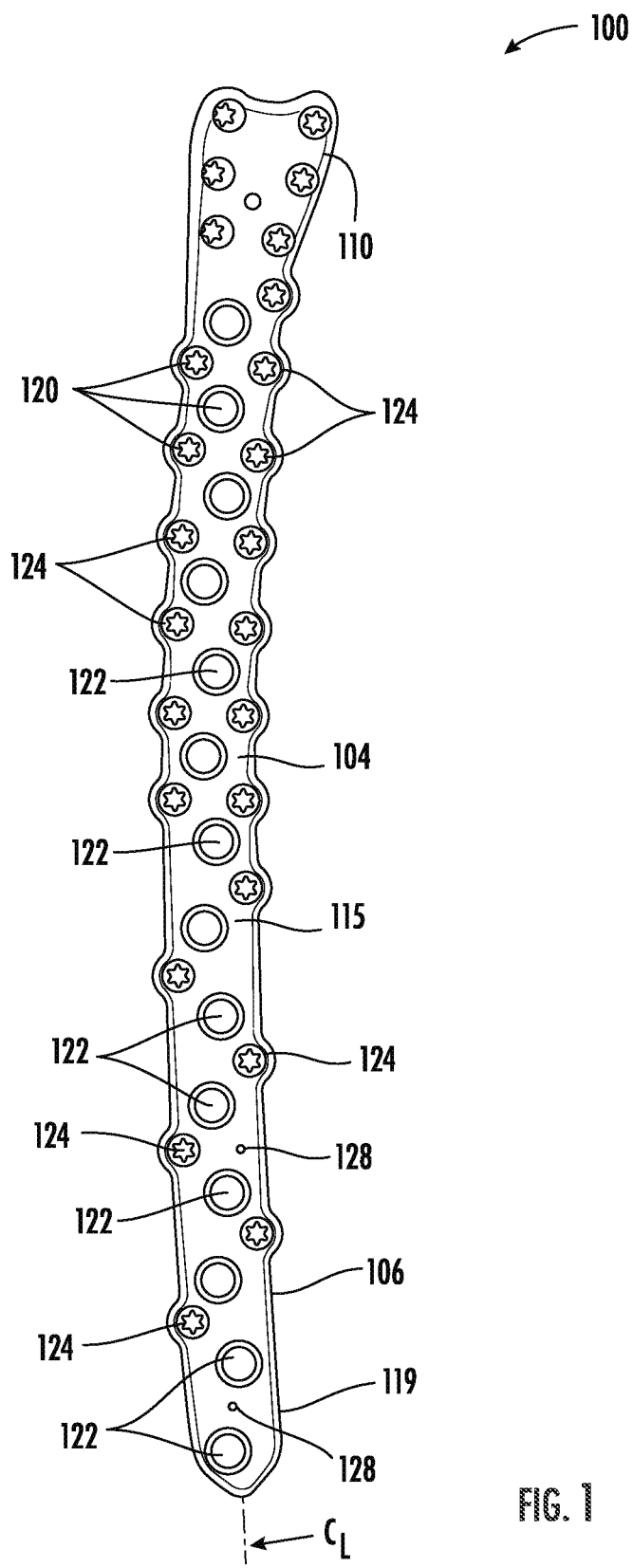
FIG. 1 is a top, perspective view of an embodiment of a periprosthetic bone plate.
Figure 2:
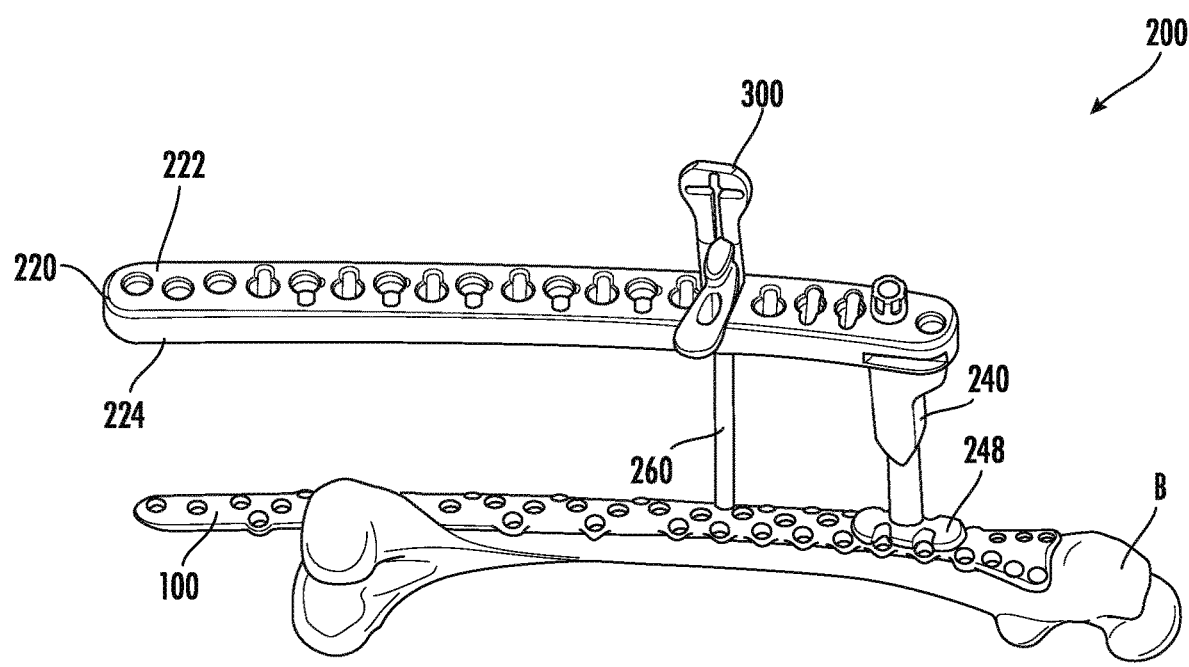
FIG. 2 is a perspective view of an embodiment of a targeting system in accordance with one or more features of the present disclosure, the targeting system shown coupled to the periprosthetic bone plate of FIG. 1 positioned adjacent to a patient's bone.
Figure 3:
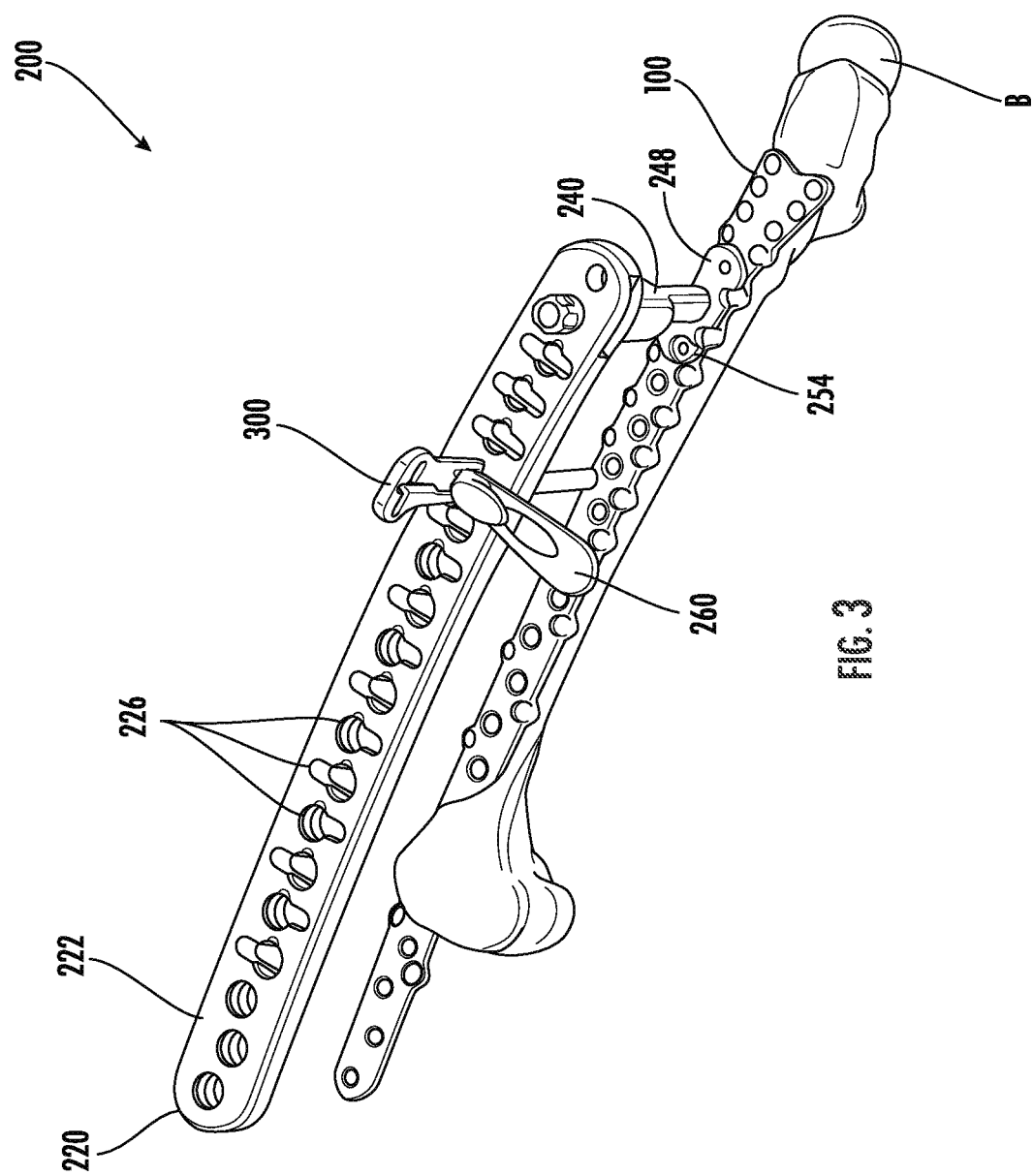
FIG. 3 is a top, perspective view of the targeting system of FIG. 2.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of a targeting system arranged and configured to be used with an orthopedic bone fixation plate will now be described more fully hereinafter with reference to the accompanying drawings, in which one or more features of the targeting system will be shown and described. It should be appreciated that the various features may be used independently of, or in combination, with each other. It will be appreciated that a targeting system as disclosed herein may be embodied in many different forms and should not be construed as being limited to the embodiments set forth herein. Rather, these embodiments are provided so that this disclosure will convey certain features of the targeting system to those skilled in the art.

Periprosthetic fractures pose unique fixation challenges. For example, the previous surgically implanted orthopedic device or implant may interfere with the placement and/or securement of a subsequent bone fixation plate. For example, in one scenario, an IM nail or stem portion of the previous surgically implanted orthopedic device or implant may interfere with positioning of the bone fixation plate and/or placement of the bone fasteners, screws, or the like (terms used interchangeably herein without the intent to limit) used to secure the bone fixation plate to the patient's bone. In addition, deterioration of the patient's bone surrounding the previous surgically implanted orthopedic device or implant via, for example, osteoporosis, defects in the bone, etc. may further complicate securement and positioning of the bone fixation plate to the patient's bone. As a result, periprosthetic fractures and the corresponding techniques for treating periprosthetic fractures are generally more difficult, with limited options.

As such, referring to FIG. 1, a bone fixation plate 100 including one or more features that has been designed and configured to provide increased flexibility in enabling a surgeon to position and secure the bone fixation plate across a fracture in a patient's bone adjacent to a previous surgically implanted orthopedic device or implant is disclosed (e.g., a periprosthetic bone plate). As illustrated, the periprosthetic bone plate 100 may be arranged and configured for positioning adjacent to a proximal femur of a patient. However, the present disclosure is not so limited, and the periprosthetic bone plate may be provided in any suitable shape and/or configuration, which, as will be appreciated by one of ordinary skill in the art, may be dependent on the location and type of patient's bone being fixed. For example, the periprosthetic bone plate may include a bone conforming arcuate surface. In addition, the bone fixation plate may be arranged and configured to span, contact, etc. a distal femur, a proximal femur, a distal tibia, a proximal tibia, a proximal humerus, a distal humerus, a fibula, an ulna, a radius, a distal radius, bones of the foot, or bones of the hand, shaft fractures on long bones, etc.

As illustrated, and as will be described herein, the periprosthetic bone plate 100 includes one or more features arranged and configured to facilitate positioning and securement to a patient's bone, which previously was implanted with a surgical orthopedic implant or device such as, for example, an IM nail, a hip prosthetic, etc.

In one embodiment, the periprosthetic bone plate 100 may include an underside, lower, or bone facing surface (terms used interchangeably herein without the intent to limit) and an upper surface 104. In addition, the periprosthetic bone plate 100 includes a head portion 110 and a shaft portion 115. Moreover, the periprosthetic proximal femur bone fixation plate 100 includes a plurality of openings 120 formed therein for receiving a plurality of fasteners (not shown) for coupling the periprosthetic bone plate 100 to the patient's bone.

In one embodiment, the openings 120 may be in the form of a locking screw (or fastener) opening 122 or a variable angled opening or variable angled fastener (or screw) opening 124 (terms used interchangeably herein without the intent to limit). That is, as will be appreciated by one of ordinary skill in the art, locking screw openings 122 may include a plurality of threads formed on an inner surface thereof for mating with threads formed on an outer surface of a head portion of a bone fastener. Thus arranged, the bone fastener may be said to be locked to the periprosthetic bone plate 100 via the locking screw openings 122. That is, as will be appreciated by one of ordinary skill in the art, the bone fastener is threaded through one of the locking screw openings 122 formed in the periprosthetic bone plate 100 and into the patient's bone. The bone fastener is secured to the periprosthetic bone plate 100 via threads formed on the head portion of the bone fastener that cooperate with the threaded locking screw opening 122 formed in the periprosthetic bone plate 100. This secures the periprosthetic bone plate 100 with respect to the patient's bone and provides rigid fixation between the periprosthetic bone plate 100 and the bone fasteners. That is, because the head portion of the bone fastener interdigitates with the threads formed in the locking screw openings 122 of the periprosthetic bone plate 100, the plate 100 and the fasteners form a stable system or construct, and the stability of the fracture can be dependent on or aided by the stiffness of the construct. Locking a bone fastener into the periprosthetic bone plate 100 can achieve angular and axial stability and eliminate the possibility for the bone fastener to toggle, slide, or be dislodged, reducing the risk of postoperative loss of reduction.

As previously mentioned, the periprosthetic bone plate 100 also includes a plurality of variable angled openings 124 formed therein for receiving a non-locking or variable angled (e.g., polyaxial) bone fastener. In use, the variable angled openings 124 are arranged and configured to enable the bone fastener inserted therein to achieve a greater range of insertion angles as compared to, for example, a conventional locking screw that is threadably coupled to the periprosthetic bone plate 100. For example, in one embodiment, the angular position of the bone fastener may be rotated through a range of approximately ±15 degrees, although the range of allowable polyaxial rotation can vary, including greater and less than the fifteen degrees. In use, the variable angled openings 124 may be provided in any suitable manner, configuration, etc. now known or hereafter developed for enabling polyaxial positioning or angling of the bone fastener relative to the periprosthetic bone plate 100.

As shown, in one embodiment, the variable angled openings 124 may include fins or projections that extend radially inward from an inner surface of the variable angled openings 124 and into an interior region of the variable angled openings 124, and which are configured to engage or cooperate with the head portion of the bone fastener. In use, the fins engage the head portion of the bone fastener in order to secure the bone fastener at a desired position and at a desired angular orientation within the variable angled opening 124. Additional information on the operation and configuration of the fins can be found in U.S. patent application Ser. No. 15/706,877, with an earliest filing date of Jul. 25, 2005, now U.S. Pat. No. 10,092,337 entitled "Systems and Methods for Using Polyaxial Plates"; U.S. patent application Ser. No. 13/524,506, filed on Jun. 15, 2012, entitled "Variable Angle Locking Implant", and International PCT Patent Application No. PCT/US20/35729, filed on Jun. 2, 2020, entitled "Orthopedic Implant with Improved Variable Angle Locking Mechanism", the entire contents of which are hereby incorporated by reference.

In one embodiment, the locking screw openings 122 may be arranged and configured to receive larger diameter bone fasteners relative to the variable angled openings 124. That is, for example, the locking screw openings 122 may be arranged and configured to receive 4.5 mm bone fasteners while the variable angled openings 124 may be arranged and configured to receive 3.5 mm bone fasteners, although these dimensions are merely exemplary and other dimensioned bone fasteners are envisioned. By arranging and configuring the periprosthetic bone plate 100 to receive larger diameter locking screws, the periprosthetic bone plate 100 is better able to be secured to the patient's bone. Meanwhile, by incorporating smaller, variable angled openings 124, the periprosthetic bone plate 100 is better able to facilitate positioning of the non-locking screws (e.g., polyaxial variable angled bone screws) around the previous surgically implanted orthopedic device or implant (e.g., smaller non-locking bone fasteners enable a surgeon to better navigate the previous surgically implanted orthopedic device or implant).

In addition, in one embodiment, the locking screw openings 122 may be more centrally located as compared to the variable angled openings 124 formed in the shaft portion 115 of the periprosthetic bone plate 100. For example, in one embodiment, the shaft portion 115 may include a central longitudinal axis CL, the locking screw openings 122 may be positioned substantially along and/or adjacent to the central longitudinal axis CL of the shaft portion 115 of the periprosthetic bone plate 100 while the variable angled openings 124 formed in the shaft portion 115, as illustrated, may be positioned along and/or adjacent to an outer periphery or surface 106 of the shaft portion 115 of the periprosthetic bone plate 100. That is, the locking screw openings 122 are positioned more interior, closer to the central longitudinal axis CL of the shaft portion 115 relative to the variable angled openings 124, which are positioned closer to the outer periphery or perimeter surface 106 of the shaft portion 115.

Thus arranged, by positioning the variable angled openings 124 along and/or adjacent to the outer periphery 106 of the shaft portion 115, the periprosthetic bone plate 100 is better able to position the variable angled bone fasteners to avoid the previous surgically implanted orthopedic device or implant (e.g., the surgeon is better able to position and insert one or more bone fasteners through the variable angled openings 124 formed in the periprosthetic bone plate 100 while avoiding, for example, the stem portion or IM nail of a previous surgically implanted orthopedic device or implant in the patient's proximal femur).

In use, the periprosthetic bone plate 100 may be provided in various lengths for repairing fractures in a patient's bone. In addition, the fastener openings may be provided in any configuration. For example, the periprosthetic bone plate 100 may include first and second regions formed in the shaft portion of the periprosthetic bone plate 100, the first and second portions including different number and/or configurations of openings 120. In addition, and/or alternatively, the periprosthetic bone plate 100 may include any now known or hereafter developed additional features such as, for example, one or more openings or slots designed to receive, for example, surgical implantation tools, different fasteners (e.g., non-locking fasteners), or the like; one or more undercuts or grooves formed in the underside or bone facing surface to provide clearance for a cable to pass underneath the periprosthetic bone plate 100, the undercuts or grooves may be incidence with or collocated with the variable angled openings 124 formed in the shaft portion 115 of the periprosthetic bone plate 100; thinning (e.g., a reduced or tapering cross-sectional area) adjacent to a distal end portion 119 (e.g., end portion opposite the head portion 110) of the periprosthetic bone plate 100 to facilitate contouring of the distal end portion 119 relative to the patient's anatomy; one or more counterbores formed in the underside or bone facing surface of the distal most locking screw openings formed in the shaft portion 115 of the periprosthetic bone plate 100 for use with an instrument to grab and compress the bone fracture; a plurality of K-wire openings 128 for enabling a K-wire to pass therethrough; etc.

As will be appreciated by one of ordinary skill in the art, the number of undercuts, variable angled openings, locking screw openings, etc. will be variable between the various bone fixation plates depending on the length of the plate.

In addition, and/or alternatively, the periprosthetic bone plate 100 may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultrahigh molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some embodiments, the bone fastener may be manufactured from the same material as the bone fixation plate. In other embodiments, the fasteners may be manufactured from a different material as compared to the bone fixation plate.

The fastener can be any type of fastener now known or hereafter developed. For example, the fastener may include any type of external thread including standard or non-standard threads. For example, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking screws, the head portion of the fastener can include any surface that will engage with and seat within a locking screw opening formed in the bone fixation plates. For example, the head portion can include threads. Alternatively, the head portion can include a series of dimples, ridges, bumps, textured areas, or any other surface that can secure the fastener.

The fastener may be any fastener now known or hereafter developed, made out of any appropriate material now known or hereafter developed. The fastener may include a bore for receiving a driver in order to drive the fastener through the bone fixation plate and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener through the bone fixation plate and into the patient's bone.

The shaft of the fastener may be fully threaded, partially threaded, or a helical blade, and/or may include one or more tacks, deployable talons, expandable elements, or any feature that allows the shaft to engage the patient's bone. It is also possible that shaft be non-threaded so that the fastener takes the form of a peg or a pin. This alternative implementation may be preferred in certain procedures where, for instance, the main goal is to prevent tilting of a bone segment or in procedures where there is no concern of the fastener pulling out from the patient's bone and hence no need for the shaft to be threaded or otherwise configured to engage the patient's bone. The end of the shaft may be a self-tapping or self-drilling tip.

Additional information on periprosthetic bone plates 100 can be found in International PCT Patent Application No. PCT/US20/57829, filed on Oct. 29, 2020, entitled "Periprosthetic Bone Plate Systems" and International PCT Patent Application No. PCT/US21/32709, filed on May 17, 2021, entitled "Periprosthetic Bone Plate", the entire contents of which are hereby incorporated by reference.

In any event, as will be readily apparent from the remaining disclosure, the focus of the present disclosure is on example embodiments of a targeting system for targeting (e.g., locating) the fastener openings formed in a bone plate. More particularly, on a targeting system for targeting (e.g., locating) the smaller, diameter variable angled openings formed in the periphery of a periprosthetic bone plate such as, for example, the variable angled openings 124 formed in the periprosthetic bone plate 100. That is, as previously described herein, the periprosthetic bone plate 100 includes a plurality of smaller diameter, variable angled openings 124 formed along the periphery of the plate 100 in the region where a previously implanted surgical implant may obstruct the placement of a larger diameter locking screw along the central axis of the plate 100. Targeting the periphery openings, more particularly, the smaller diameter variable angled openings 124 formed in the periphery of the periprosthetic bone plate 100, may be problematic (e.g., percutaneously inserting the screws or fasteners may be challenging for some surgeons).

Thus, as will be described herein, in accordance with one or more features of the present disclosure, a targeting system is disclosed. The targeting system being arranged and configured to assist the surgeon in locating the variable angled openings 124 formed in the periphery of the periprosthetic bone plate 100 (e.g., the targeting system is arranged and configured to facilitate targeting, aiming, identifying, locating, etc. (terms used interchangeably herein without the intent to limit) one or more of the smaller, variable angled openings 124 in the periprosthetic bone plate 100. In use, in one embodiment, the targeting system enables a surgeon to percutaneously locate and insert a bone fastener into the smaller, variable angled openings 124 in the periprosthetic bone plate 100. In this manner, an open incision may be avoided resulting in less trauma and quicker patient recovery.

Referring to FIGS. 2-5, in one embodiment, the targeting system 200 includes an alignment guide or targeter 220, a targeter handle 240 arranged and configured to couple the alignment guide 220 to the periprosthetic bone plate 100, a surgical instrument 260 (e.g., a trocar, a drill guide, and/or a screw guide), and a plug 300.

Figure 6:
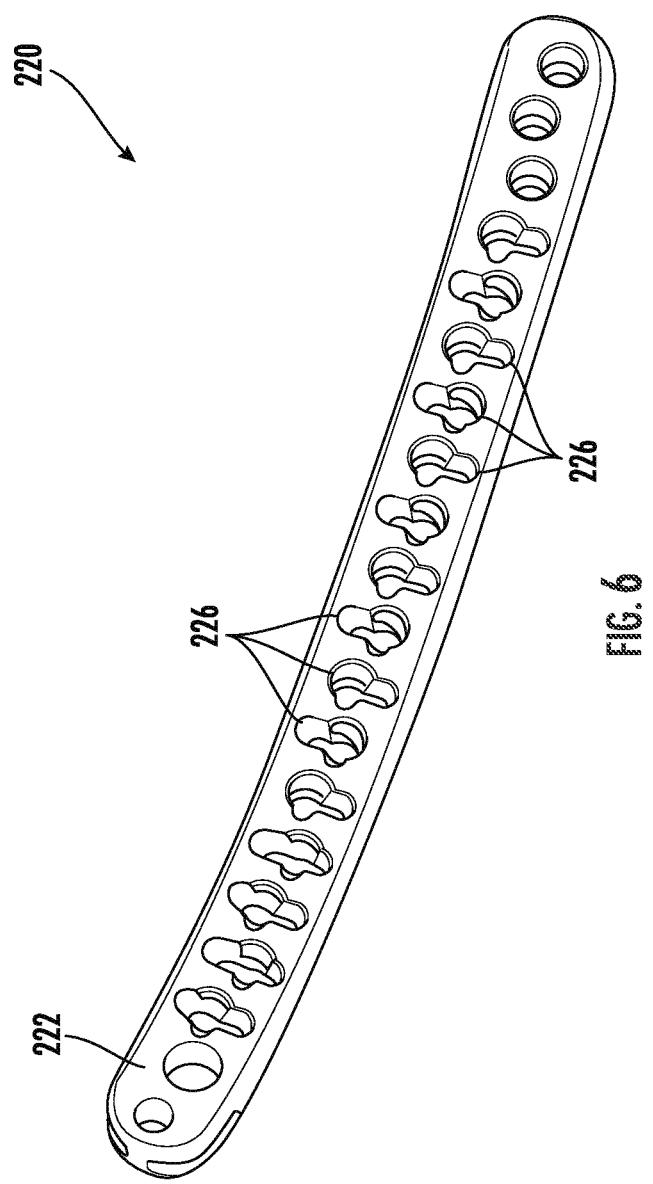
FIG. 6 is a perspective view of an embodiment of an alignment guide in accordance with one or more features of the present disclosure, the alignment guide being one component of the targeting system of FIG. 2.

With additional reference to FIG. 6, in one embodiment, the alignment guide 220 includes a top surface 222, a bottom surface 224 (FIGS. 2 and 5), and a plurality of openings 226 extending therethrough. As illustrated, in one embodiment, the openings 226 may be in the form of threaded circular openings and/or non-threaded circular openings. In addition, as illustrated, one or more of the openings 226 may be in the form of a combo-slot (e.g., combination of an enlarged circular opening and elongated slot extending from one or both sides thereof, as such, in one embodiment, the openings 226 may be provided in the form of a keyhole, although this is but one configuration). In use, one or more surgical instruments 260 can be inserted through the openings 226 to assist the surgeon in drilling and/or positioning the fasteners into the openings 120 formed in the periprosthetic bone plate 100.

Figure 7A:
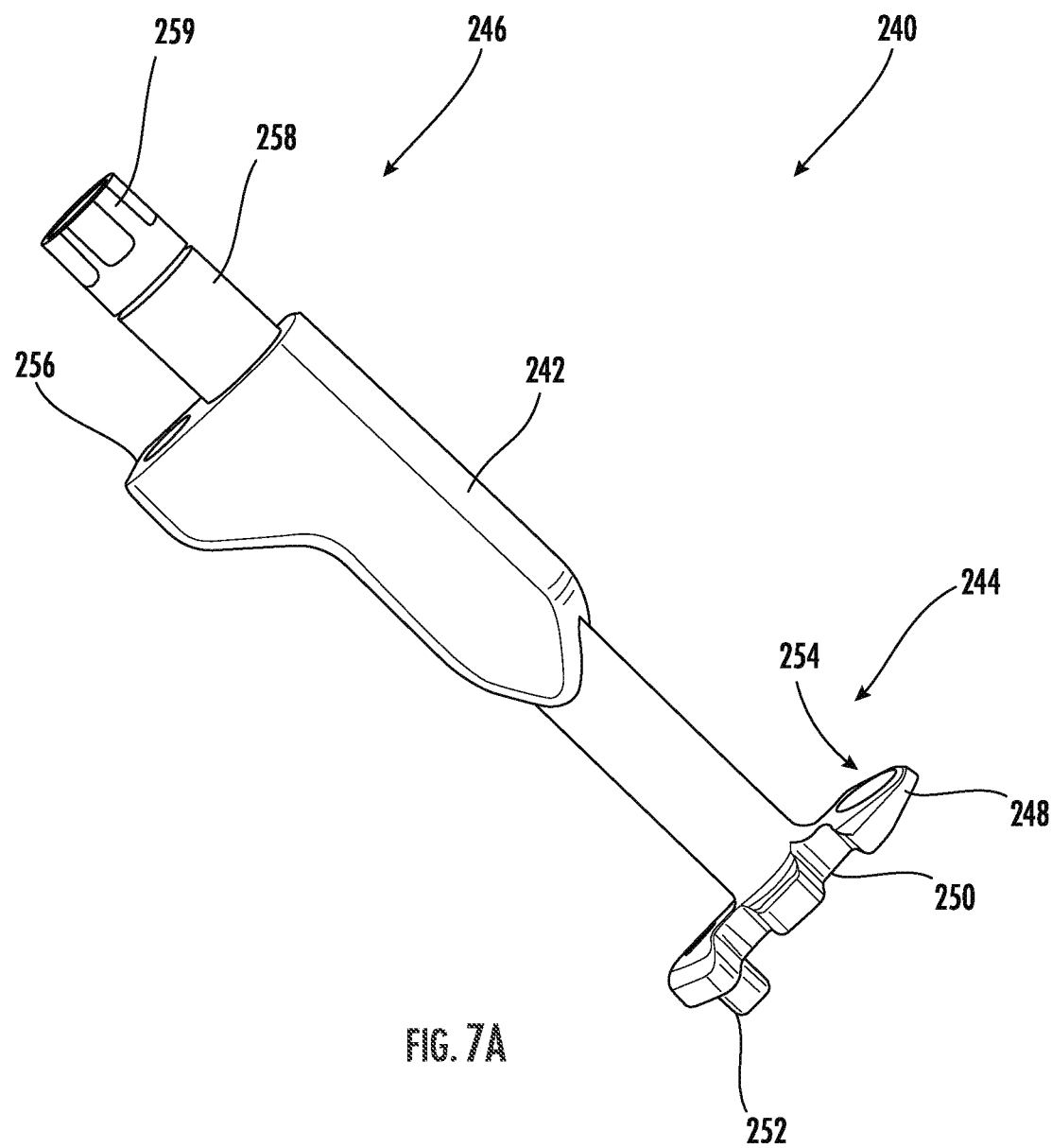
FIG. 7A is a perspective view of an embodiment of a targeter handle in accordance with one or more features of the present disclosure, the targeter handle being one component of the targeting system of FIG. 2.

With additional reference to FIG. 7A, in one embodiment, the targeter handle 240 is arranged and configured to couple the alignment guide 220 to the periprosthetic bone plate 100. As illustrated, in one embodiment, the targeter handle 240 may include a body member 242 including a distal end 244 and a proximal end 246. In use, the distal end 244 may include an elongated plate-like end portion 248. The elongated plate-like end portion 248 may include a distal end surface 250 arranged and configured to contact the top surface 104 of the periprosthetic bone plate 100. In addition, the elongated plate-like end portion 248 may include a projection 252 extending therefrom. In use, the projection 252 is arranged and configured to be positioned within one of the openings 120 formed in the periprosthetic bone plate 100. As illustrated, the elongated plate-like end portion 248 may also include one or more openings 254 (FIGS. 3 and 7A) formed therein. In use, the one or more openings 254 may be arranged and configured to align with one or more of the locking screw openings 122 formed in the periprosthetic bone plate 100 so that a locking screw may be positioned through the opening 254 formed in the elongated plate-like end portion 248 and into the locking screw opening 122 formed in the periprosthetic bone plate 100. In addition, the periphery surface of the elongated plate-like end portion 248 may be contoured to facilitate alignment, access, etc. to the variable angled openings 124 formed in the periphery of the periprosthetic bone plate 100. In this manner, the elongated plate-like end portion 248 enables access to the variable angled openings 124 while maintaining a low profile (e.g., profile of the elongated plate-like end portion 248 does not extend beyond the periphery surface of the periprosthetic bone plate 100 to minimize patient's trauma). However, it should be appreciated that this is but one configuration, the targeter handle 240 may have any other now known or hereafter developed configuration arranged and configured to couple the alignment guide 220 to the periprosthetic bone plate 100.

As illustrated, in one embodiment, the proximal end 246 of the targeter handle 240 includes a bearing surface 256 and a proximal projection or stem 258. In use, the bottom surface of the alignment guide 220 is arranged and configured to be seated on the bearing surface 256. Meanwhile, the proximal projection or stem 258 is arranged and configured to extend through an opening (e.g., a non-threaded circular opening) formed in the alignment guide 220. Thus arranged, the alignment guide 220 can be coupled to the proximal end 246 of the targeter handle 240 while the distal end 244 of the targeter handle 240 is coupled to the periprosthetic bone plate 100. It should be appreciated that the alignment guide 220 could be coupled to the targeter handle 240 by any other suitable mechanism now known or hereafter developed. For example, in one embodiment, the targeter handle 240 and the alignment guide 220 could be monolithically or integrally formed.

Figure 7B:
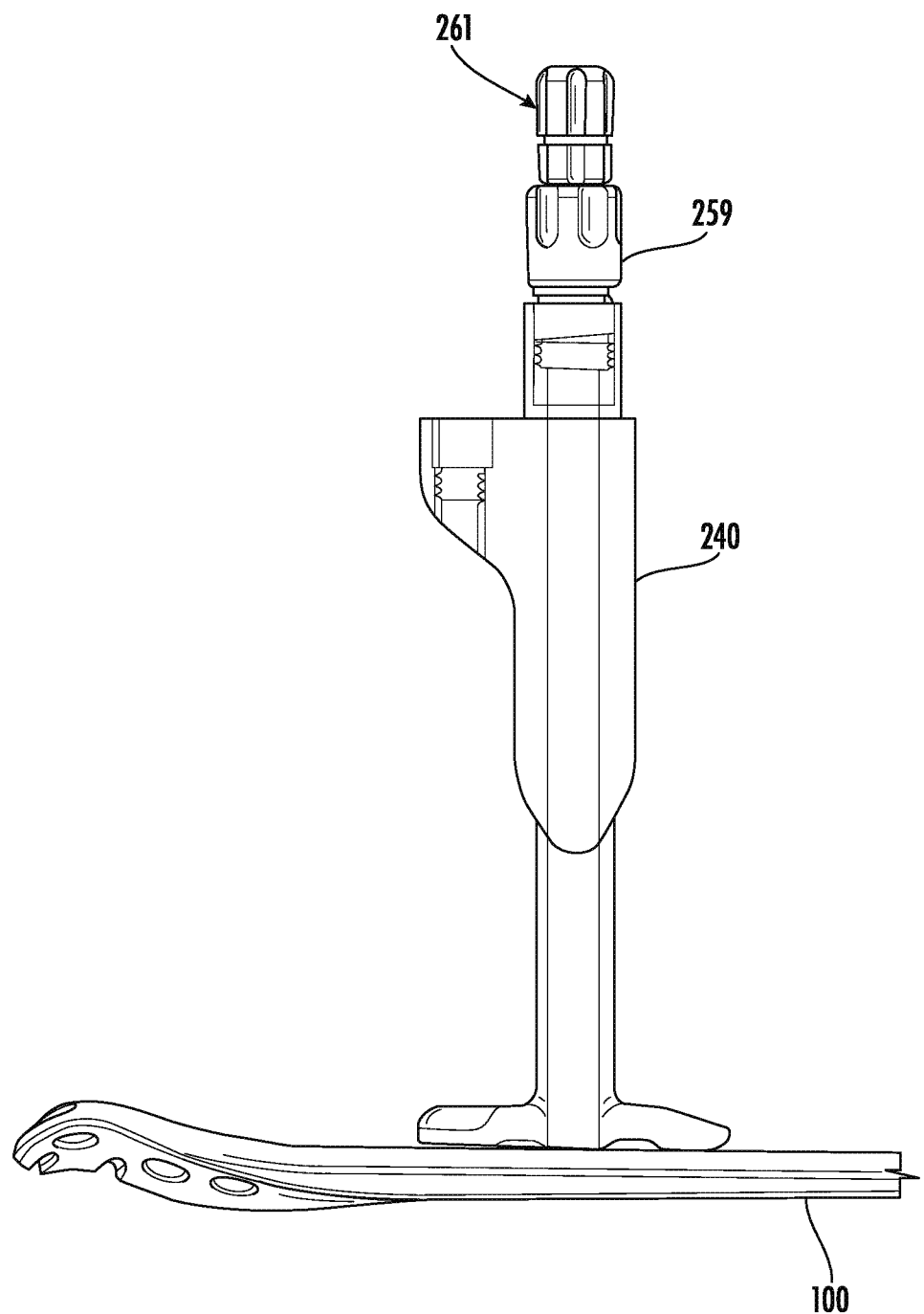
FIG. 7B is a side view of the targeter handle of FIG. 7A coupled to a bone plate in accordance with one or more features of the present disclosure.
Figure 8:
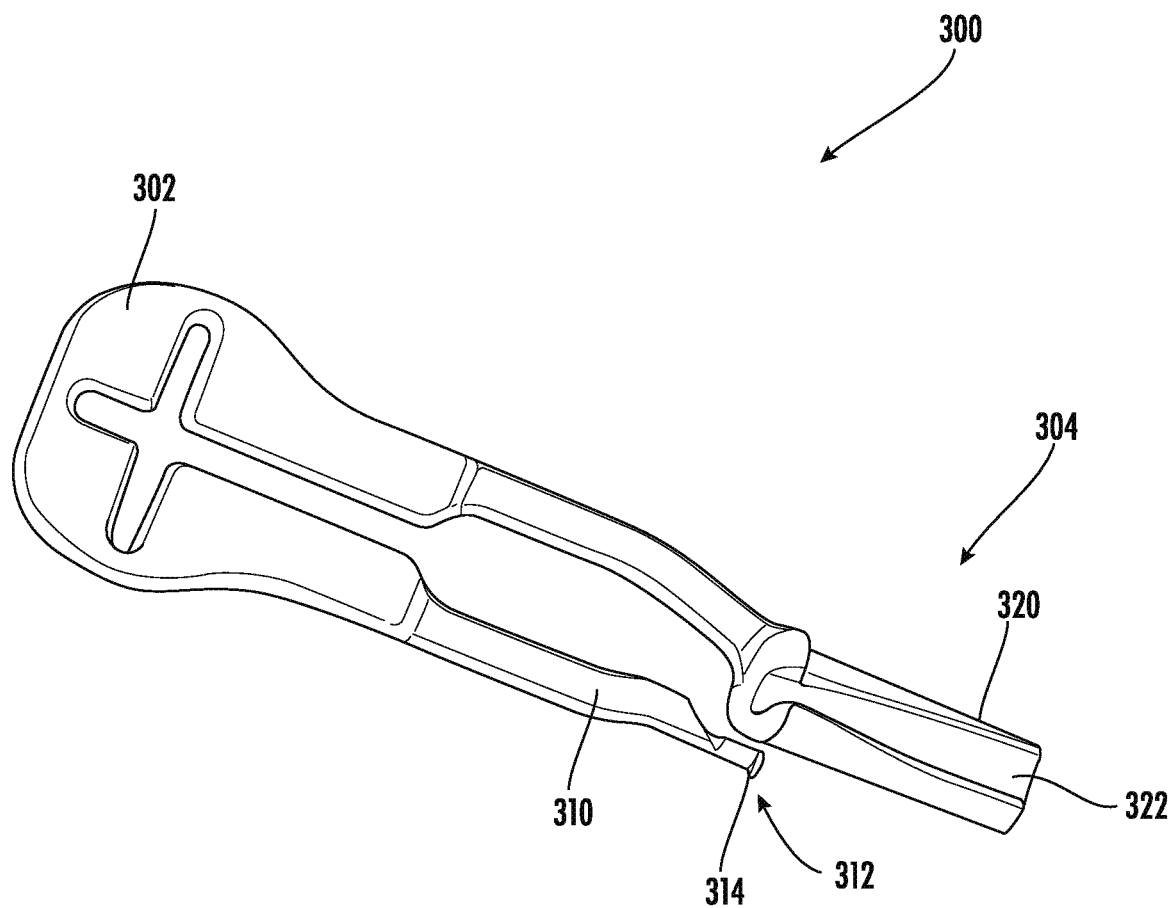
FIG. 8 is a perspective view of an embodiment of a plug in accordance with one or more features of the present disclosure, the plug being one component of the targeting system of FIG. 2.
Figure 9:
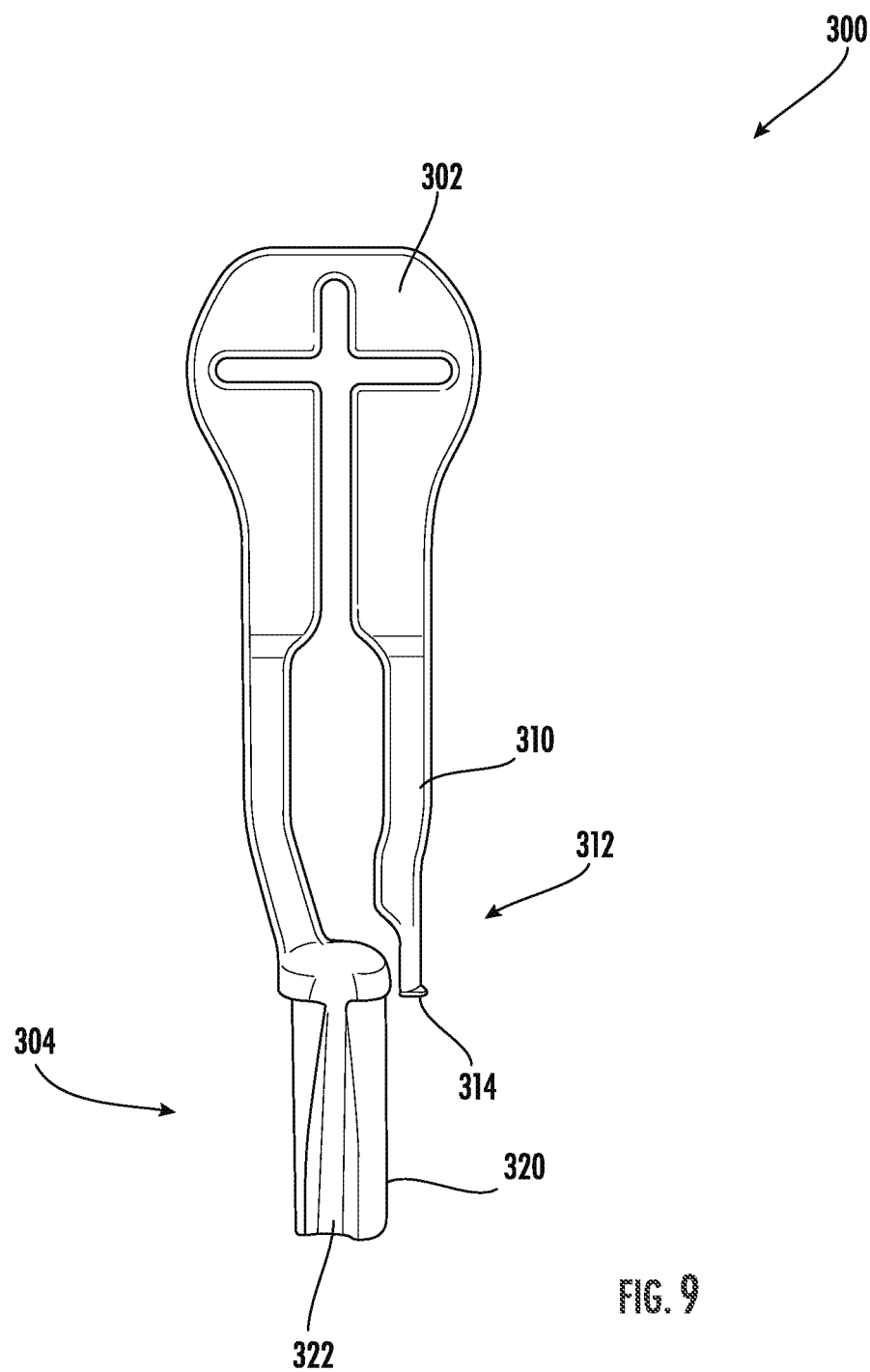
FIG. 9 is an alternate view of the plug of FIG. 8.

In one embodiment, with additional reference to FIG. 7B, the proximal projection or stem 258 may include an internally threaded bore for receiving an externally threaded end cap 259. In use, the externally threaded end cap 259 is arranged and configured to hold the handle 260 against the bone plate 100 while, for example, an inner drill sleeve is inserted therethrough (e.g., prevents the handle from dislodging while, for example, the inner drill sleeve is inserted therein). That is, for example, as shown, a drill guide 261 may be inserted through the cannulation formed in the end cap 259 and the cannulation in the handle 240. As such, the drill guide 261 can be threaded into the bone plate 100. By unthreading the end cap 259, the handle 240 remains buttressed between the bone plate 100 and the drill guide 261. It should be appreciated that the end cap could be coupled to the stem 258 by any other suitable mechanism now known or hereafter developed including, for example, press-fitted, molded, etc.

As illustrated, in one embodiment, the targeter handle 240 may be monolithically or integrally formed. Alternatively, however, the targeter handle 240 may be manufactured from multiple components, which may be then coupled together.

Figure 4:
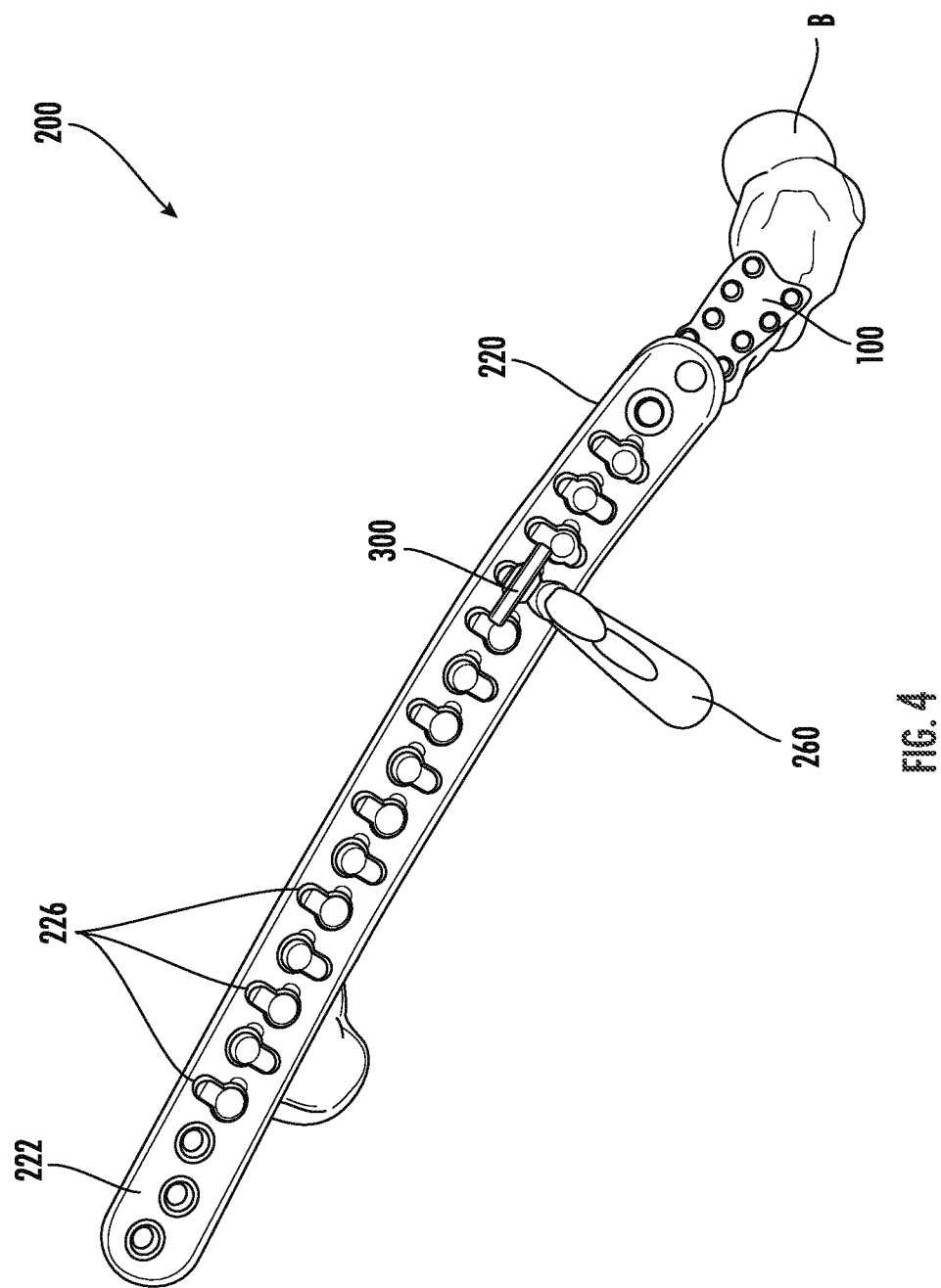
FIG. 4 is an alternate top, perspective view of the targeting system of FIG. 2.
Figure 5:
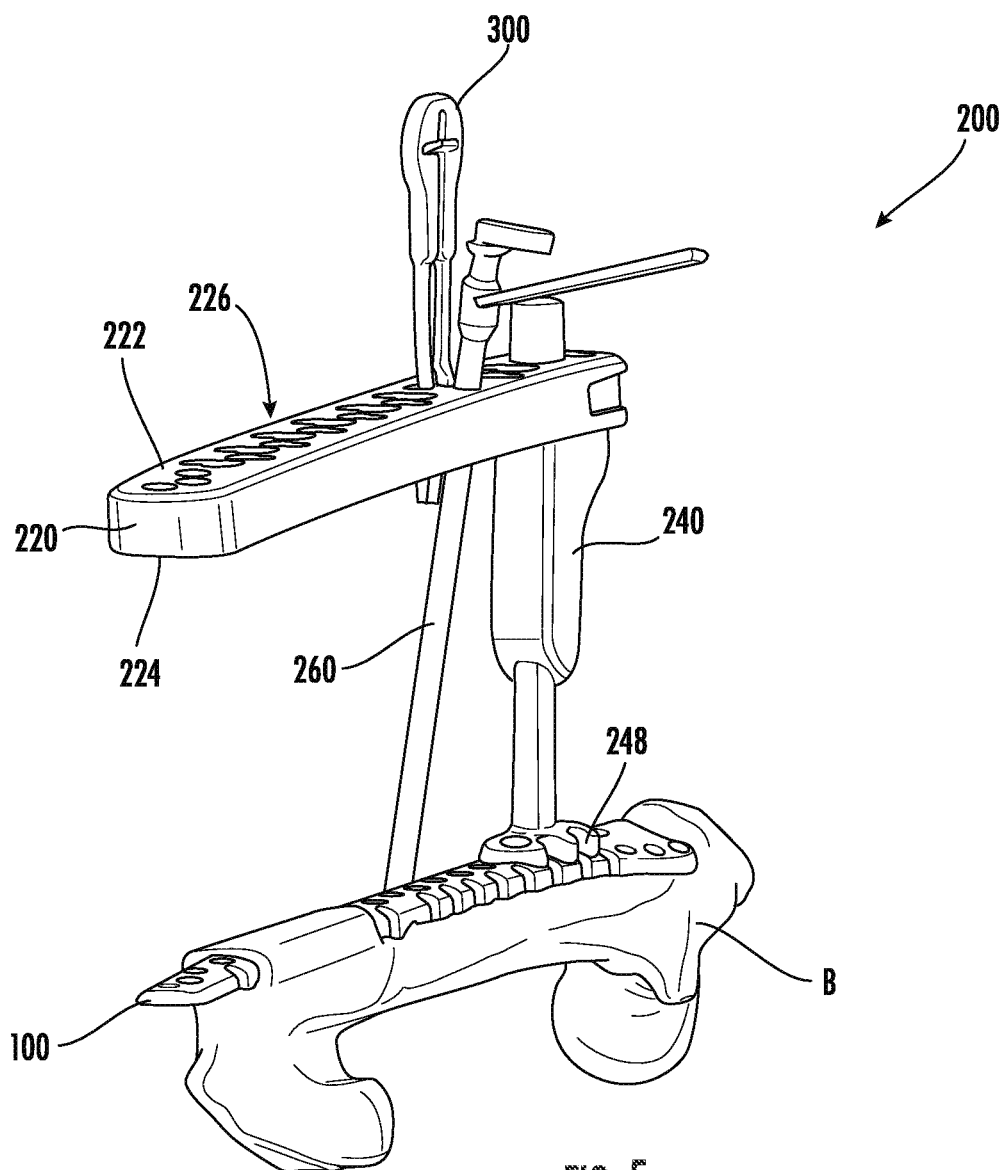
FIG. 5 is an alternate perspective view of the targeting system of FIG. 2.

As best illustrated in FIG. 4, with the alignment guide 220 coupled to the periprosthetic bone plate 100, the enlarged central portion of the combo-slots 226 are aligned with the more-centrally located, larger diameter locking screw openings 122 formed in the periprosthetic bone plate 100. In addition, the elongated slotted portion of the combo-slots 226 enable access to the variable angled openings 124 formed in the periphery of the periprosthetic bone plate 100.

As illustrated in FIGS. 2-5, 11, and 12, in accordance with one or more features of the present disclosure, the plug 300 may be positioned within the combo-slot 226 formed in the alignment guide 220 (e.g., within the enlarged central portion of the combo-slots 226). As will be described in greater detail herein, by positioning the plug 300 into the enlarged central portion of the combo-slots 226, the elongated slotted portion of the combo-slot 226 is transformed or reduced to a substantially circular hole or opening with a predefined trajectory aligned with one of the variable angled openings 124 formed in the periphery of the periprosthetic bone plate 100. That is, insertion of the plug 300 into the enlarged central portion of the combo-slot 226 closes or blocks off the enlarged central portion of the combo-slot 226 formed in the alignment guide 220 thereby transforming the elongated slotted portion of the combo-slot 226 into a circular hole or opening aligned with one of the variable angled openings 124 formed in the periphery of the periprosthetic bone plate 100 via a predefined trajectory. Thus arranged, a surgical instrument 260 such as, for example, a trocar, a drill guide, and/or a screw guide, can be inserted into the circular opening defined by the slotted-portion of the combo-slot 226 and the plug 300.

In one embodiment, the surgical instrument 260 can be inserted until the distal end of the surgical instrument 260 contacts or engages the variable angled opening 124 formed in the periphery of the periprosthetic bone plate 100. In this manner, the opening defined by the combination of the slotted portion of the combo-slot 226 and the plug 300 provides a defined opening that allows surgeons to easily target the variable angled openings 124 formed in the periprosthetic bone plate 100. Moreover, once properly targeted and with the surgical instruments 260 coupled to the periprosthetic bone plate 100, the plug 300 can be removed from the alignment guide 220 enabling the surgeon to manipulate, move, angle, etc. the surgical instrument 260 relative to the periprosthetic bone plate 100 to thereby allow freedom to adjust the trajectory of the surgical instrument 260 within the permissible range of the variable angled opening 124 while engagement of the distal end of the surgical instrument 260 with the periprosthetic bone plate 100 prevents, or at least greatly minimizes, the surgical instrument 260 from dislodging from the periprosthetic bone plate 100.

Figure 13:
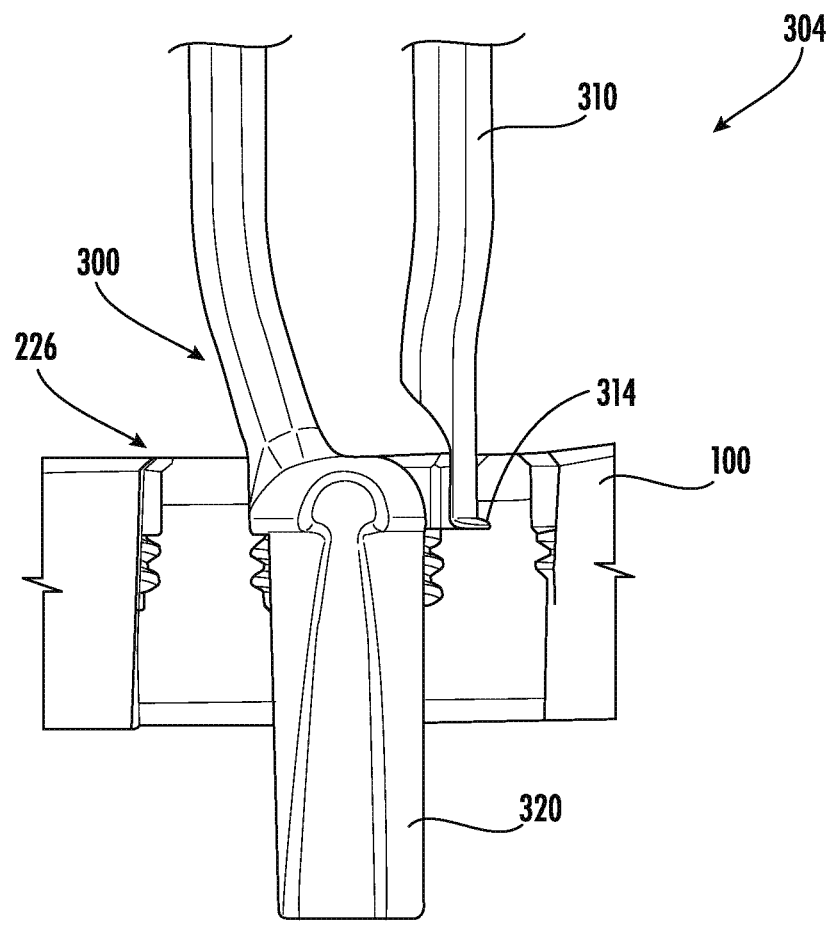
FIG. 13 is a detailed, cross-sectional view of the targeting system of FIG. 2 illustrating the plug positioned within a combo-slot formed in the alignment guide in accordance with one or more features of the present disclosure.

Referring to FIGS. 8-10B, in one embodiment, the plug 300 includes a proximal end portion 302 and a distal end portion 304. As illustrated, the proximal end portion 302 is arranged and configured to be grasped by a user. The distal end portion 304 is arranged and configured to be positioned within the enlarged central portion of the combo-slot 226 formed in the alignment guide 220. In addition, as illustrated, the plug 300 may include a flexible arm 310 (e.g., a flexible, cantilevered arm) extending from the proximal end portion 302 towards the distal end portion 304. In use, the distal end portion 312 of the flexible, cantilevered arm 310 is arranged and configured to grasp the enlarged central portion of the combo-slot 226 formed in the alignment guide 220. Thus arranged, the plug 300 can be coupled to the alignment guide 220. Subsequently, by flexing the plug 300 (e.g., pressing or compressing the flexible, cantilevered arm 310), the plug 300 can be easily removed from the enlarged central portion of the combo-slot 226 formed in the alignment guide 220. In use, the flexible, cantilever arm 310 may be arranged and configured to mate with the combo-slot 226 formed in the alignment guide 220 to prevent unintentional decoupling of the plug 300 from the alignment guide 220. For example, in one embodiment, the cantilevered arm 310 may include a geometry or projection 314 arranged and configured to mate with a keyway and/or undercut formed in the alignment guide 220 as best illustrated in FIG. 13.

Figure 11:
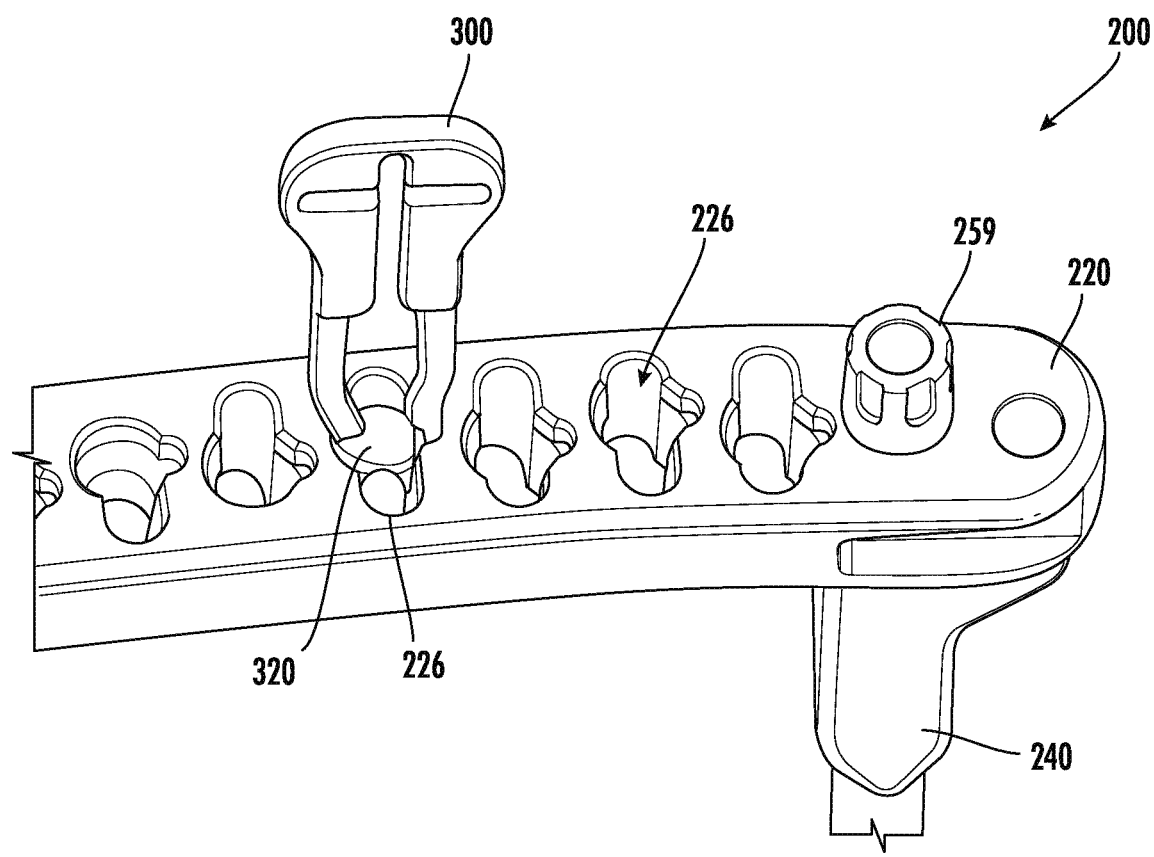
FIG. 11 is a detailed, perspective view of the targeting system of FIG. 2 illustrating the plug positioned within a combo-slot formed in the alignment guide in accordance with one or more features of the present disclosure.
Figure 12:
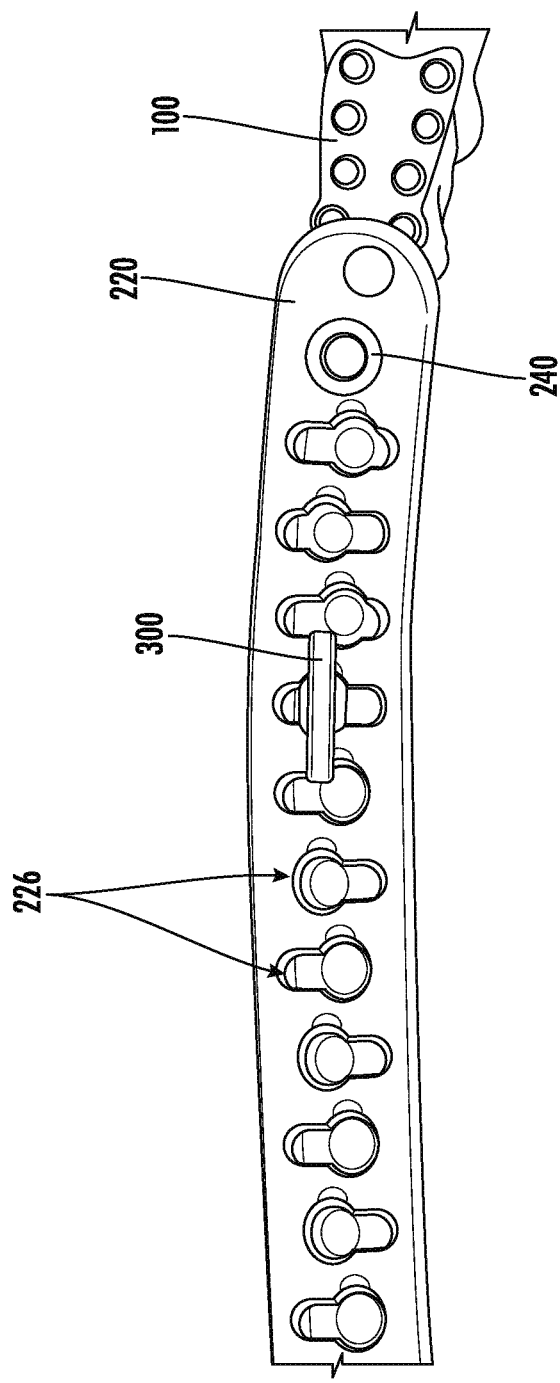
FIG. 12 is a top, perspective view of the targeting system of FIG. 2 illustrating the plug positioned within a combo-slot formed in the alignment guide in accordance with one or more features of the present disclosure.

As illustrated in FIGS. 8-10B and 13, in one embodiment, the distal end portion 304 may be in the form of a circular projection 320 arranged and configured to be received within the enlarged central portion of the combo-slot 226 formed in the alignment guide 220. In addition, the circular projection 320 may include a longitudinal groove, a notch, a radiused surface, etc. 322 (terms used interchangeably herein without the intent to limit). In one embodiment, the notch 322 is arranged and configured to correspond with the radius of the combo-slot 226. In use, as best illustrated in FIGS. 11 and 12, when positioned within the combo-slot 226 formed in the alignment guide 220, the circular projection 320 of the distal end portion 304 of the plug 300 transforms the combo-slot 226 into a hole with a predefined trajectory to one of the variable angled openings 124 formed in the periphery of the periprosthetic bone plate 100. That is, insertion of the plug 300 into the combo-slot 226 closes or blocks off the enlarged central portion of the combo-slot 226 formed in the alignment guide 220 thereby transforming the slotted portion of the combo-slot 226 into a circular opening thereby facilitating easier insertion of the surgical instruments 260 (e.g., surgical instruments are more readily positioned within the opening defined by the plug 300 and the combo-slot 226 and guided to the variable angled opening 124 formed in the periprosthetic bone plate 100).

Figures 10A, 10B:
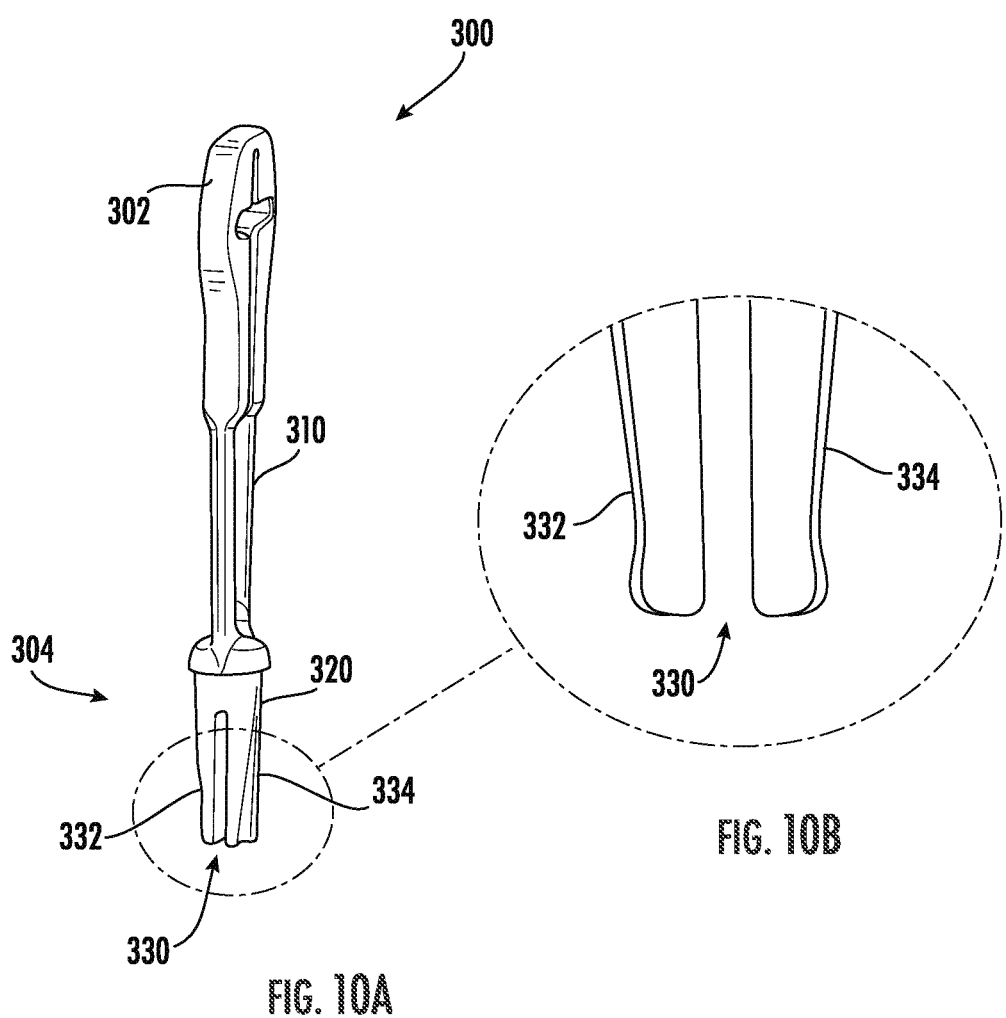
FIG. 10A is an alternate view of the plug of FIG. 8.
FIG. 10B is a detailed view of a distal portion of the plug of FIG. 8.

Referring to FIGS. 10A and 10B, in one embodiment, the circular projection 320 of the distal end portion 304 of the plug 300 may include a slot or cutout 330 formed therein. The slot or cutout 330 extending from the distal end. Thus arranged, the circular projection 320 of the distal end portion 304 of the plug 300 may include first and second flexible arms 332, 334. Moreover, referring to FIG. 10B, in one embodiment, the tip of the first and second flexible arms 332, 334 may be arranged and configured with a kick arranged and configured to bias the plug 300 toward the centerline of the alignment guide 220. In use, the kick biases the surgical instrument 260 toward the centerline of the periprosthetic bone plate 100 to enable improved alignment. For example, in one embodiment, the kick may be in the form of a taper arranged and configured to bias the plug 300 toward the centerline of the alignment guide 220.

Figure 14:
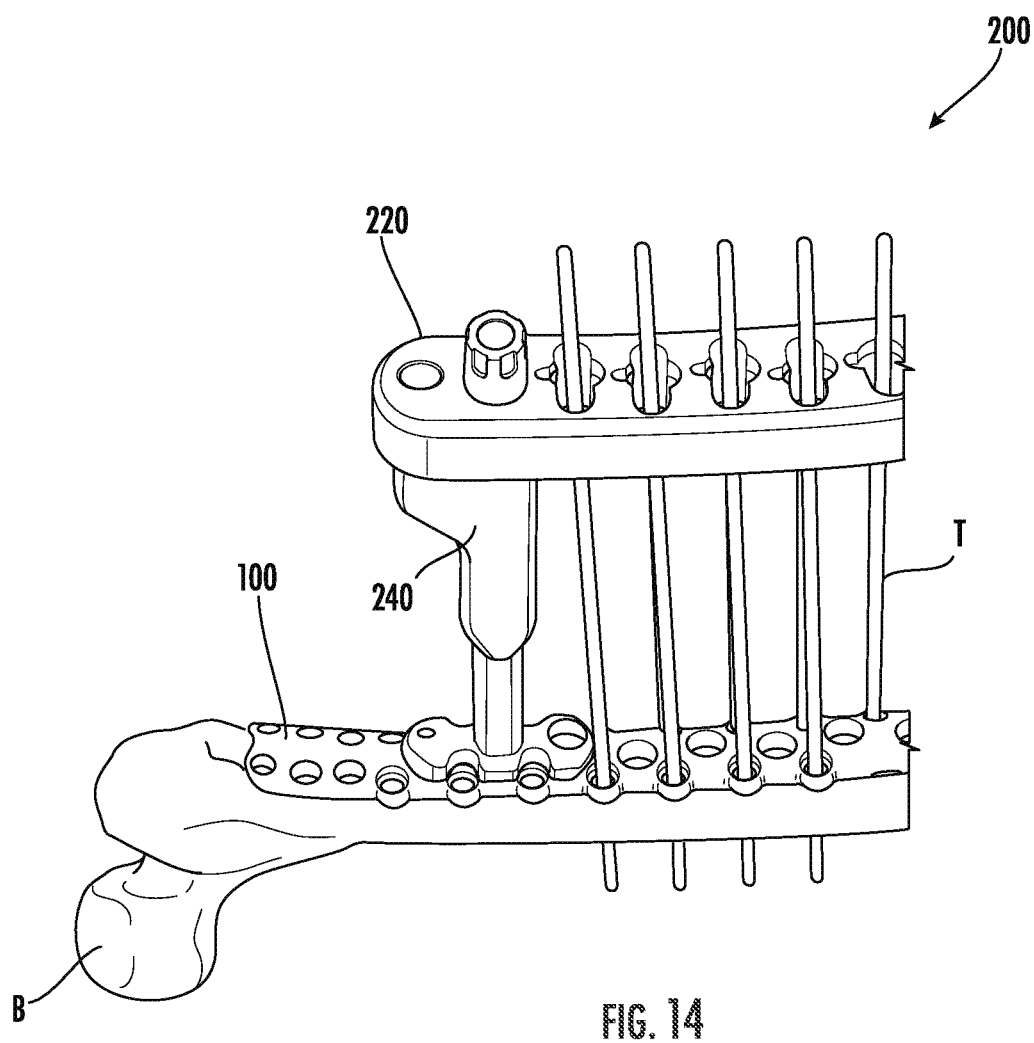
FIG. 14 is a detailed, perspective view of the targeting system of FIG. 2 illustrating a predefined trajectory extending between the alignment guide and the periprosthetic bone plate.

In use, referring to FIG. 14, the alignment guide 220 and the plug 300 are arranged and configured such that the alignment or trajectory T through the circular opening defined by the slotted portion of the combo-slot 226 and the distal end portion 304 of the plug 300 to the variable angled openings 124 formed in the periphery of the periprosthetic bone plate 100 places the surgical instrument 260 at a divergent angle from the central axis of the patient's bone B to thereby assist in avoiding any previous surgically implanted orthopedic implant.

In use, as will be described in greater detail below, the surgical instrument 260 is preferably inserted until a distal end of the surgical instrument 260 contacts the variable angled opening 124 formed in the periprosthetic bone plate 100. Thus arranged, once the surgical instrument 260 is coupled to the periprosthetic bone plate 100, the plug 300 can be removed from the alignment guide 220 so that angular flexibility of the surgical instrument 260 relative to the variable angled opening 124 is permissible. Once proper positioning of the placement of the fastener is determined, the surgical instrument 260 can be utilized to, for example, drill the fastener opening into the patient's bone B, guide the fastener into the patient's bone B, etc. That is, utilizing the plug 300 assists the user in identifying, locating, etc. the trajectory T to the variable angled opening 124 formed in the periprosthetic bone plate 100 so that the surgical instrument 260 can be coupled to the periprosthetic bone plate 100. Once the surgical instrument 260 has been coupled to the periprosthetic bone plate 100, the plug 300 may be removed thereby providing the user with an extra degree of freedom in selecting the proper trajectory T of the fastener.

The surgical instrument 260 may be any now known or hereafter developed surgical instrument used and configured to insert a bone fastener. For example, in one embodiment, the surgical instrument 260 may be a trocar, a drill guide, and/or a screw guide.

In one embodiment, as will be readily appreciated by one of ordinary skill in the art, the trocar, drill guide, and screw guide may be assembled together. Next, the combined surgical instrument 260 can be inserted along the predefined trajectory T through the opening defined by the plug 300 and the combo-slot 226 and the variable angled opening 124 formed in the periprosthetic bone plate 100. In one embodiment, the drill guide and the screw guide may include an interface arranged and configured to prevent disassembly of the surgical instrument 260 when pressure is applied to the distal end of the drill guide. For example, the feature may be in the form of a threaded connection between the drill guide and the screw guide. Alternatively, the feature may be in the form of a spring mechanism that compresses when inserted into the screw guide and subsequently expand when the drill guide is properly positioned relative to the screw guide.

Figure 15:
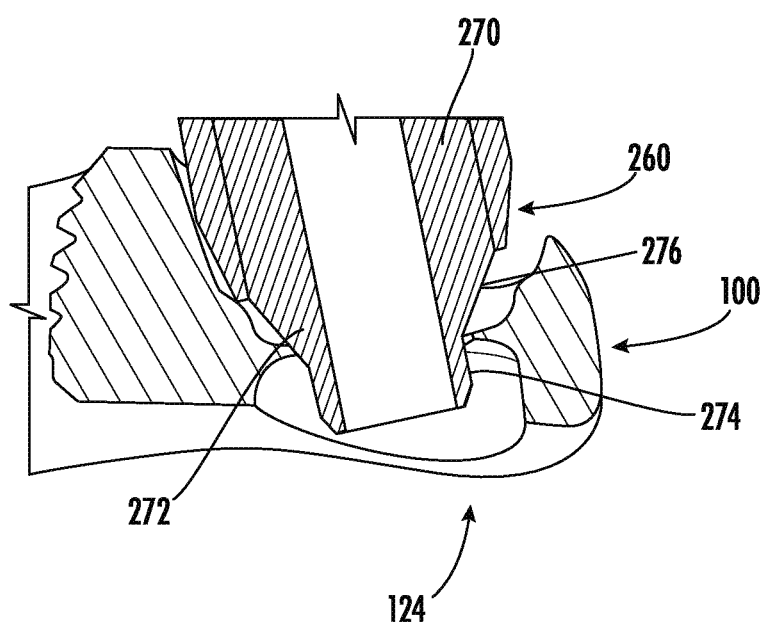
FIG. 15 is a detailed, cross-sectional view of a surgical instrument positioned within a variable angled opening formed in the periprosthetic bone plate in accordance with one or more features of the present disclosure.

Referring to FIG. 15, in one embodiment, the screw guide is arranged and configured with a geometry that optimizes accuracy of the positioning of the screw guide relative to the variable angled opening 124 formed in the periprosthetic bone plate 100. For example, as illustrated, in one embodiment, the portion of the screw guide sits over a cone feature in the periprosthetic bone plate 100. The drill guide portion of the guide nest inside the tabs of the variable angled opening 124 formed in the periprosthetic bone plate 100 and protects the variable angled feature from damage when a drill is inserted. In addition, as illustrated, in one embodiment, the surgical instrument 260 or drill guide 270 includes a body portion having a distal tip 272. The distal tip 272 includes a cylindrical section 274 and a tapered section 276. The tapered section 276 being positioned between the cylindrical section 274 and the body. In one embodiment, the cylindrical section 274 has a length, as measured from the distal end of the drill guide 270 to the tapered section 276, that is shorter than the length of the tapered section 276. Thus arranged, it has been found that the surgical instrument and/or sleeve thereof can be better anchored within the variable angle opening 124 of the periprosthetic bone plate 100 while the surgeon adjusts the angle of the drill guide (e.g., provides better engagement of the surgical instrument to the bone plate to prevent the surgical instrument from being pulled out during repositioning).

In one example method of use, the periprosthetic bone plate 100 may be coupled to the alignment guide 220 via the targeter handle 240. Next, the surgeon may insert the periprosthetic bone plate 100 percutaneously through a small incision in the patient's skin (e.g., 5 to 6 cm incision to allow the periprosthetic bone plate 100 to be inserted and slide under the patient's skin). Alternatively, the targeter handle 240 may be initially coupled to the periprosthetic bone plate 100, which may then be percutaneously inserted through a small incision. Once properly positioned, the alignment guide 220 may be coupled to the proximal end 246 of the targeter handle 240. As needed, the patient's bone fracture may be initially reduced and the periprosthetic bone plate 100 may be coupled to the patient's bone B via, for example, one or more locking screws. Additional, fine-tuning reduction may be performed and finally the bone plate 100 may be completely fixed to the patient's bone B.

In accordance with features of the present disclosure, during coupling of the bone plate 100 to the patient's bone B, the plug 300 may be inserted into one of the combo-slots 226 formed in the alignment guide 220 to close or transform the combo-slot 226 into a hole with a predefined trajectory T aligned with one of the variable angled openings 124 formed in the periphery of the periprosthetic bone plate 100. One or more surgical instruments may then be inserted through the hole created by the slotted portion of the combo-slot 226 and the plug 300. In one embodiment, the surgical instruments 260 may be inserted until the distal end thereof contacts the periprosthetic bone plate 100. The plug 300 can then be removed for the alignment guide 220 allowing the surgical instruments 260 to move freely. Once an acceptable trajectory is found, a drill can be inserted to create the pathway into the bone B. The drill guide can then be removed and a screwdriver with a screw can be inserted into bone B thereby coupling the bone plate to the patient's bone.

While the present disclosure has been described and illustrated for use in targeting a smaller diameter, variable angled opening formed in a periphery of the periprosthetic bone plate 100, it should be appreciated that the targeting system may have other uses such as, for example, targeting one or more openings formed in an intermedullary nail or a plate and intermedullary nail. Thus, the present disclosure should not be limited to any particular implant (e.g., bone plate) unless specifically claimed.

The foregoing description has broad application. Accordingly, the discussion of any embodiment is meant only to be explanatory and is not intended to suggest that the scope of the disclosure, including the claims, is limited to these example embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order, and relative sizes reflected in the drawings attached hereto may vary.

The invention claimed is:

1. A targeting system arranged and configured to target a variable angled opening in a periprosthetic bone plate to facilitate insertion of a bone fastener into the variable angled opening, the targeting system comprising:
    an alignment guide arranged and configured to couple to the periprosthetic bone plate, the alignment guide including a plurality of combo-slots formed therein, each combo-slot including an enlarged central portion and an elongated slot extending from the enlarged central portion; and
    a plug selectively positionable within one of the plurality of combo-slots formed in the alignment guide, in use, the plug is positioned within the enlarged central portion of the combo-slot to prevent access to the enlarged central portion, the plug defining an opening encompassing the elongated slot and a portion of the plug, the opening having a defined trajectory to the variable angled opening formed in the periprosthetic bone plate.

2. The targeting system of claim 1, further comprising a surgical instrument positionable within the opening defined by the plug and the combo-slot of the alignment guide, a distal end of the surgical instrument being arranged and configured to couple to the variable angled opening formed in the periprosthetic bone plate in use.

3. The targeting system of claim 2, wherein, once the distal end of the surgical instrument has been coupled to the variable angled opening formed in the periprosthetic bone plate, the plug is selectively removable from the opening to enable additional freedom in positioning the surgical instrument relative to the variable angled opening formed in the periprosthetic bone plate.

4. The targeting system of claim 2, wherein the distal end of the surgical instrument includes a distal tip arranged and configured to be received within the variable angled opening formed in the periprosthetic bone plate, the distal tip including a cylindrical section and a tapered section, the tapered section being positioned between the cylindrical section and an intermediate body portion of the surgical instrument.

5. The targeting system of claim 1, wherein positioning the plug within the enlarged central portion of the combo-slot transforms the combo-slot into a circular opening aligned with one of the plurality of variable angled openings formed in the periprosthetic bone plate.

6. The targeting system of claim 1, further comprising a targeter handle arranged and configured to couple the alignment guide to the periprosthetic bone plate, the targeter handle including a distal end arranged and configured to couple to the periprosthetic bone plate and a proximal end arranged and configured to couple to the alignment guide.

7. The targeting system of claim 6, wherein the distal end of the targeter handle is arranged and configured to contact a top surface of the periprosthetic bone plate, the distal end of the targeter handle including a projection arranged and configured to be positioned within an opening formed in the periprosthetic bone plate.

8. The targeting system of claim 7, wherein the distal end of the targeter handle includes an elongated plate-like end portion including a distal surface arranged and configured to contact the top surface of the periprosthetic bone plate, the projection extending from the distal surface.

9. The targeting system of claim 8, wherein the elongated plate-like end portion includes one or more openings arranged and configured to align with one or more locking screw openings formed in the periprosthetic bone plate, and one or more contours formed along a periphery of the elongated plate-like end portion arranged and configured to facilitate access to the variable angled openings formed in the periprosthetic bone plate.

10. The targeting system of claim 6, wherein the proximal end of the targeter handle includes a bearing surface and a proximal projection, the bearing surface being arranged and configured to enable a bottom surface of the alignment guide to be seated thereon, the proximal projection being arranged and configured to extend through an opening formed in the alignment guide.

11. The targeting system of claim 1, wherein the plug includes a distal end portion including a circular projection arranged and configured to be received within the enlarged central portion of the combo-slot formed in the alignment guide.

12. The targeting system of claim 11, wherein the circular projection includes a notch formed therein, the notch being arranged and configured to correspond with a radius of the elongated slotted portion of the combo-slot, wherein, with the circular projection positioned within the enlarged central portion of the combo-slot, the notch partially defines the opening.

13. The targeting system of claim 12, wherein the circular projection includes a slot extending from a distal end thereof, the slot defining first and second flexible arms.

14. The targeting system of claim 13, wherein the first and second flexible arms are arranged and configured with a kick to bias the plug toward a centerline of the alignment guide.

15. The targeting system claim 1, wherein the plug includes a cantilever arm extending from a proximal end thereof towards a distal end thereof, the flexible arm including a distal end arranged and configured to engage the enlarged central portion of the combo-slot formed in the alignment guide to couple the plug to the alignment guide.

16. The targeting system of claim 15, wherein the cantilevered arm includes a laterally extending projection arranged and configured to mate with a keyway formed in the enlarged central portion of the combo-slot formed in the alignment guide.

17. The targeting system claim 1, further comprising a periprosthetic bone plate including a central longitudinal axis, an outer periphery surface, a plurality of threaded locking screw openings arranged and configured to receive a plurality of locking screws, respectively, and a plurality of variable angled openings arranged and configured to receive a plurality of variable angled screws, respectively, the plurality of variable angled openings are positioned along the outer periphery surface of the bone plate, the plurality of locking screw openings are positioned closer to the central longitudinal axis of the bone plate.

18. A targeting system arranged and configured to target a variable angled opening in a periprosthetic bone plate to facilitate insertion of a bone fastener into the variable angled opening, the targeting system comprising:
  an alignment guide arranged and configured to couple to the periprosthetic bone plate, the alignment guide including a plurality of combo-slots formed therein, each combo-slot including an enlarged central portion and an elongated slot extending from the enlarged central portion; and
  a plug selectively positionable within one of the plurality of combo-slots formed in the alignment guide, the plug positionable within the enlarged central portion of the combo-slot to define an opening through the alignment guide having a defined trajectory to the variable angled opening formed in the periprosthetic bone plate;
  wherein the plug includes a distal end portion including a circular projection arranged and configured to be received within the enlarged central portion of the combo-slot formed in the alignment guide; and
  wherein the circular projection includes a notch formed therein, the notch being arranged and configured to correspond with a radius of the elongated slotted portion of the combo-slot, wherein, with the circular projection positioned within the enlarged central portion of the combo-slot, the notch partially defines the opening.

19. The targeting system of claim 18, wherein the circular projection includes a slot extending from a distal end thereof, the slot defining first and second flexible arms.

20. The targeting system of claim 19, wherein the first and second flexible arms are arranged and configured with a kick to bias the plug toward a centerline of the alignment guide.

21. A targeting system arranged and configured to target a variable angled opening in a periprosthetic bone plate to facilitate insertion of a bone fastener into the variable angled opening, the targeting system comprising:
  an alignment guide arranged and configured to couple to the periprosthetic bone plate, the alignment guide including a plurality of combo-slots formed therein, each combo-slot including an enlarged central portion and an elongated slot extending from the enlarged central portion; and a plug selectively positionable within one of the plurality of combo-slots formed in the alignment guide, the plug positionable within the enlarged central portion of the combo-slot to define an opening through the alignment guide having a defined trajectory to the variable angled opening formed in the periprosthetic bone plate;

wherein the plug includes a cantilever arm extending from a proximal end thereof towards a distal end thereof, the flexible arm including a distal end arranged and configured to engage the enlarged central portion of the combo-slot formed in the alignment guide to couple the plug to the alignment guide.

22. The targeting system of claim 21, wherein the cantilevered arm includes a laterally extending projection arranged and configured to mate with a keyway formed in the enlarged central portion of the combo-slot formed in the alignment guide.

* * * * *